(12) United States Patent
Park et al.

(10) Patent No.: US 10,874,354 B2
(45) Date of Patent: Dec. 29, 2020

(54) APPARATUS AND METHOD FOR BIOMETRIC INFORMATION DETECTION

(71) Applicant: SAMSUNG ELECTRONICS CO., LTD., Suwon-si (KR)

(72) Inventors: Jin Young Park, Hwaseong-si (KR); Hyeong Seok Jang, Gimcheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 720 days.

(21) Appl. No.: 15/395,578

(22) Filed: Dec. 30, 2016

(65) Prior Publication Data

US 2018/0042557 A1 Feb. 15, 2018

(30) Foreign Application Priority Data

Aug. 10, 2016 (KR) .................. 10-2016-0101919

(51) Int. Cl.
*A61B 5/00* (2006.01)
*A61B 5/053* (2006.01)

(52) U.S. Cl.
CPC .......... *A61B 5/7221* (2013.01); *A61B 5/0075* (2013.01); *A61B 5/0531* (2013.01); *A61B 5/6822* (2013.01); *A61B 5/6823* (2013.01); *A61B 5/6824* (2013.01); *A61B 5/6826* (2013.01); *A61B 5/6828* (2013.01); *A61B 5/6829* (2013.01); *A61B 5/6831* (2013.01); *A61B 5/6843* (2013.01); *A61B 5/7232* (2013.01); *A61B 5/441* (2013.01);
(Continued)

(58) Field of Classification Search
CPC ......... A61B 5/00; A61B 5/053; A61B 5/6841; A61B 5/0059; A61B 5/489

USPC ........................... 600/300, 476, 547
See application file for complete search history.

(56) References Cited

U.S. PATENT DOCUMENTS 7,103,407 B2 9/2006 Hjelt et al.
7,133,710 B2 11/2006 Acosta et al.
(Continued)

FOREIGN PATENT DOCUMENTS

CN 104146712 A 11/2014
EP 3023069 A1 5/2016
(Continued)

OTHER PUBLICATIONS

Communication dated Sep. 25, 2017, issued by the European Patent Office in counterpart European Patent Application No. 17154176.6.
(Continued)

*Primary Examiner* — Jon Eric C Morales
(74) *Attorney, Agent, or Firm* — Sughrue Mion, PLLC

(57) ABSTRACT

An apparatus and method for biometric information detection are provided. The apparatus includes a housing, a biometric sensor disposed on a surface of the housing, and configured to detect biometric information of a subject, and an impedance measurer including biometric electrode pairs disposed around the biometric sensor, the impedance measurer being configured to measure bio-impedances of the subject using the biometric electrode pairs. The apparatus further includes a processor configured to determine a bio-impedance ratio, based on the measured bio-impedances, and determine validity of the detected biometric information, based on the determined bio-impedance ratio.

26 Claims, 13 Drawing Sheets

(52) U.S. Cl.
CPC ....... *A61B 5/681* (2013.01); *A61B 2560/0462* (2013.01); *A61B 2560/0468* (2013.01)

(56) References Cited

U.S. PATENT DOCUMENTS

| | | | |
|---|---|---|---|
| 7,299,080 | B2 | 11/2007 | Acosta et al. |
| 8,055,330 | B2 | 11/2011 | Egozi |
| 8,174,394 | B2 | 5/2012 | Ridder et al. |
| 8,195,284 | B2 | 6/2012 | Kuramori et al. |
| 8,355,767 | B2 | 1/2013 | Hunter et al. |
| 2012/0003862 | A1 | 1/2012 | Newman et al. |
| 2012/0143020 | A1 | 6/2012 | Bordoley et al. |
| 2012/0245439 | A1 | 9/2012 | Andre et al. |
| 2013/0060098 | A1 | 3/2013 | Thomsen et al. |
| 2013/0090537 | A1 | 4/2013 | Schemmann et al. |
| 2014/0031952 | A1 | 1/2014 | Harshbarger et al. |
| 2014/0201988 | A1 | 7/2014 | Wang et al. |
| 2015/0074797 | A1 | 3/2015 | Choi et al. |
| 2015/0161374 | A1 | 6/2015 | Kim |
| 2015/0190085 | A1 | 7/2015 | Nathan et al. |
| 2015/0286813 | A1 | 10/2015 | Jakobsson |
| 2015/0358043 | A1 | 12/2015 | Jeong et al. |
| 2016/0051193 | A1 | 2/2016 | Park et al. |
| 2016/0089053 | A1 | 3/2016 | Lee et al. |
| 2016/0095521 | A1 | 4/2016 | Inan et al. |
| 2016/0106337 | A1* | 4/2016 | Jung .................... A61B 5/0537 600/547 |
| 2016/0192885 | A1* | 7/2016 | Lee ...................... A61B 5/6841 600/476 |
| 2016/0324440 | A1 | 11/2016 | Kim et al. |

FOREIGN PATENT DOCUMENTS

| | | |
|---|---|---|
| JP | 2005-270546 A | 10/2005 |
| JP | 2007-195813 A | 8/2007 |
| JP | 2012-525164 A | 10/2012 |
| KR | 10-2009-0005511 A | 1/2009 |
| KR | 10-2015-0081735 A | 7/2015 |
| KR | 10-2016-0023487 A | 3/2016 |
| KR | 10-2016-0036958 A | 4/2016 |
| WO | 2011/076886 A2 | 6/2011 |

OTHER PUBLICATIONS

Team Valencell, "How Accuracy Happens in Biometric Wearables", Mar. 3, 2016, Valencell Inc., 6 pages total, http://www.valencell.com/blog/2016/03/how-accuracy-happens-in-biometric-wearables/.

* cited by examiner ically with respect to the biometric sensor, the impedance measurer may be further configured to measure a first bio-impedance of the subject using the one or more measurement electrode pairs, and measure a second bio-impedance of the subject using the reference electrode pair, and the processor may be further configured to determine a bio-impedance ratio of the measured first bio-impedance to the measured second bio-impedance.

APPARATUS AND METHOD FOR BIOMETRIC INFORMATION DETECTION

CROSS-REFERENCE TO RELATED APPLICATION

This application claims priority from Korean Patent Application No. 10-2016-0101919, filed on Aug. 10, 2016, in the Korean Intellectual Property Office, the disclosure of which is incorporated herein by reference in its entirety.

BACKGROUND

1. Field

Apparatuses and methods consistent with exemplary embodiments relate to a biometric information detection technology for measuring biometric information of a target subject and a wearable device employing the biometric information detection technology.

2. Description of Related Art

With the increasing attention on health issues, various types of biometric information detection techniques have been developed. For example, recent wearable devices are equipped with a biometric information detection sensor, which allows a user to detect his/her biometric information. According to the type of the biometric information of interest or the purpose of detection, the user may detect the biometric information for one time or periodically. The obtained biometric information may be utilized alone or in combination with other information as an index that represents a health state of the user.

Because the position or the condition for the biometric information measurement can always be varied due to the motion of the user, a biometric information detection apparatus may have to achieve accuracy or reproducibility of measurement. The reproducibility of measurement refers to repeating of the measurement under the same measurement conditions, regardless of the time or an environment where the measurement is performed. In the case in which the user conducts a measurement manually or by the use of a wearable device the user is wearing, a contact state or a facing state of a sensor to a target subject is not constant or stable, but rather very variable, and hence a demand for the accuracy or reproducibility of measurement is higher. In the case of an optical biometric information detection sensor, a received optical measurement signal may be contain noise depending on a state in which the sensor faces the target subject, and thus the facing state of the sensor may have a more significant impact on the accuracy or reproducibility of measurement.

SUMMARY

Exemplary embodiments may address at least the above problems and/or disadvantages and other disadvantages not described above. Also, the exemplary embodiments are not required to overcome the disadvantages described above, and may not overcome any of the problems described above.

According to an aspect of an exemplary embodiment, there is provided an apparatus for biometric information detection, the apparatus including a housing, a biometric sensor disposed on a surface of the housing, and configured to detect biometric information of a subject, and an impedance measurer including biometric electrode pairs disposed around the biometric sensor, the impedance measurer being configured to measure bio-impedances of the subject using the biometric electrode pairs. The apparatus further includes a processor configured to determine a bio-impedance ratio, based on the measured bio-impedances, and determine validity of the detected biometric information, based on the determined bio-impedance ratio.

The processor may be further configured to determine that the detected biometric information is valid in response to a size of the determined bio-impedance ratio or a sequential change in the determined bio-impedance ratio being within a predetermined range.

The biometric sensor may be further configured to estimate the biometric information by applying a predetermined correlation model to a biometric signal, and update the predetermined correlation model, based on the estimated biometric information in response to a sequential change in the determined bio-impedance ratio reaching a predetermined range.

The biometric electrode pairs may include one or more measurement electrode pairs and a reference electrode pair that are disposed symmetrically with respect to the biometric sensor, the impedance measurer may be further configured to measure a first bio-impedance of the subject using the one or more measurement electrode pairs, and measure a second bio-impedance of the subject using the reference electrode pair, and the processor may be further configured to determine a bio-impedance ratio of the measured first bio-impedance to the measured second bio-impedance.

The one or more measurement electrode pairs may include a measurement electrode pair disposed along a direction perpendicular to a direction along which the reference electrode pair is disposed.

The one or more measurement electrode pairs may include a measurement electrode pair disposed along a direction along which the biometric sensor is disposed.

The biometric sensor may include an optical signal detector configured to irradiate light to the subject, and receive an optical signal returning from the subject, and the processor may be further configured to estimate the biometric information, based on the received optical signal.

The processor may be further configured to determine that the received optical signal or the estimated biometric information is valid in response to the determined bio-impedance ratio being within a predetermined range.

The processor may be further configured to determine that the received optical signal or the estimated biometric information is valid in response to a sequential change in the determined bio-impedance ratio reaching a predetermined range.

According to an aspect of an exemplary embodiment, there is provided a method for biometric information detection, the method including detecting biometric information of a subject, using a biometric sensor contacting the subject, and measuring bio-impedances of the subject, using biometric electrode pairs contacting the subject. The method further includes determining a bio-impedance ratio, based on the measured bio-impedances, and determining validity of the detected biometric information, based on the determined bio-impedance ratio.

According to an aspect of an exemplary embodiment, there is provided a wearable device including a housing, a wearing member connected to the housing, and configured to allow a user to wear the wearable device, and a biometric sensor disposed on a surface of the housing, the surface contacting the user, and the biometric sensor being configured to detect biometric information of the user. The wearable device further includes an impedance measurer including a reference electrode pair and a measurement electrode pair that are disposed on the surface, the impedance measurer being configured to measure bio-impedances of the user the reference electrode pair and the measurement electrode pair, and a processor configured to determine a bio-impedance ratio of the measured bio-impedances, and determine validity of the detected biometric information, based on the determined bio-impedance ratio.

The reference electrode pair may be disposed along a first direction that is a longitudinal direction of a body part on which the user wears the wearable device.

The body part may be one of an arm, a leg, a finger, a toe, a neck, and a torso.

The reference electrode pair may be disposed symmetrically with respect to the biometric sensor.

The measurement electrode pair may be disposed along a second direction perpendicular to the first direction.

The measurement electrode pair may be disposed symmetrically with respect to the biometric sensor.

The impedance measurer may further include a second measurement electrode pair disposed along a third direction, a third measurement electrode pair disposed along a fourth direction, and a fourth measurement electrode pair disposed along a fifth direction, the second measurement electrode pair, the third measurement electrode pair, and the fourth measurement electrode pair being disposed symmetrically with respect to the biometric sensor, and the third direction forming an angle of 45 degrees with respect to the first direction, forming an angle of 45 degrees with respect to the fourth direction, and being perpendicular to the fifth direction.

The processor may be further configured to determine a state in which the user is wearing the wearable device, based on the determined bio-impedance ratio, and generate information for guiding the user to correct the determined state in response to a result of the determination of the state.

The reference electrode pair may be disposed along a direction perpendicular to a direction along which the wearing member extends from the housing, and the measurement electrode pair may be disposed along a same direction as the direction along which the wearing member extends from the housing.

The processor may be further configured to determine that the detected biometric information is valid in response to a size of the determined bio-impedance ratio or a sequential change in the determined bio-impedance ratio being within a predetermined range.

The wearable device may further include any one or any combination of an audio output interface, a display, and a communicator that are disposed in the housing, and configured to output information that is generated based on the determined bio-impedance ratio.

The biometric sensor may include an optical signal configured to irradiate light to skin of the user, and receive an optical signal returning from the skin, and the processor may be further configured to estimate the biometric information, based on the received optical signal.

The processor may be further configured to determine that the received optical signal or the estimated biometric information is valid in response to the determined bio-impedance ratio being within a predetermined range.

The processor may be further configured to determine that the received optical signal or the estimated biometric information is valid in response to a sequential change in the determined bio-impedance ratio reaching a predetermined range.

According to an aspect of an exemplary embodiment, there is provided an apparatus for biometric information detection, the apparatus including a housing, a biometric sensor disposed on a surface of the housing, and configured to detect biometric information of a subject, and an impedance measurer including first biometric electrodes and second biometric electrodes disposed on the surface, the first biometric electrodes being configured to measure a first bio-impedance of the subject, and the second biometric electrodes being configured to measure a second bio-impedance of the subject. The apparatus further includes a processor configured to determine a bio-impedance ratio of the measured first bio-impedance to the measured second bio-impedance, and determine whether the detected biometric information is valid, based on the determined bio-impedance ratio.

One of the first biometric electrodes may be disposed on a first side of the biometric sensor, and another one of the first biometric electrodes may be disposed on a second side of the biometric sensor, the second side being symmetrically opposite the first side.

One of the second biometric electrodes may be disposed on a first side of the biometric sensor, and another one of the second biometric electrodes may be disposed on a second side of the biometric sensor, the second side being symmetrically opposite the first side.

The first biometric electrodes and the second biometric electrodes may be disposed along a first direction, and the impedance measurer may further include third biometric electrodes disposed along a second direction, and fourth biometric electrodes disposed along a third direction, the second direction forming a first angle with respect to the first direction, and third direction forming a second angle with respect to the first direction.

BRIEF DESCRIPTION OF THE DRAWINGS

The above and/or other aspects will be more apparent by describing exemplary embodiments with reference to the accompanying drawings.

DETAILED DESCRIPTION

Figure 1A:
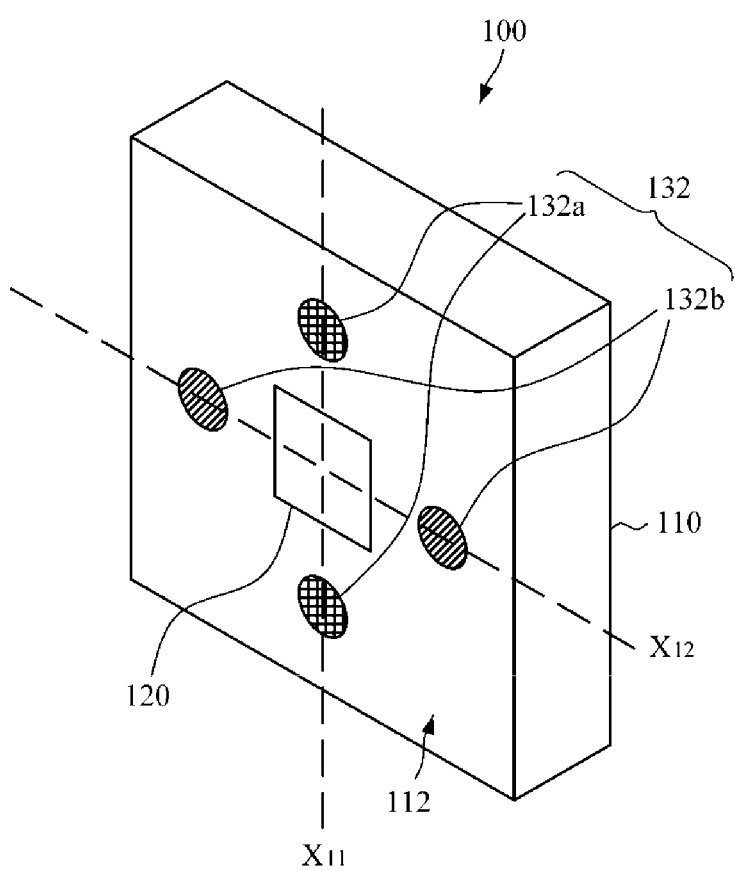
FIG. 1A is a perspective view of an apparatus for biometric information detection, according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions may not be described in detail because they would obscure the description with unnecessary detail.

Figure 1B:
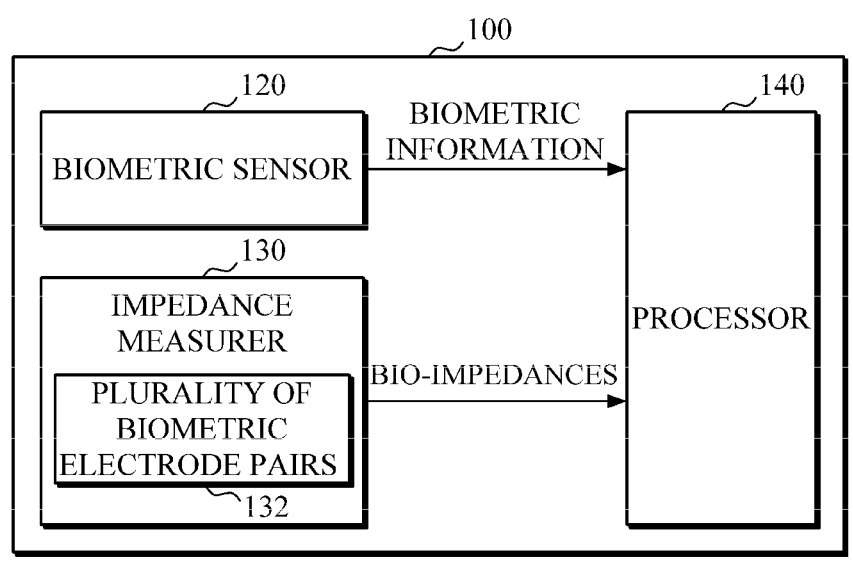
FIG. 1B is a block diagram of elements that are equipped in or mounted in a housing of the apparatus of FIG. 1A.

FIG. 1A is a perspective view of an apparatus 100 for biometric information detection, according to an exemplary embodiment, and FIG. 1B is a block diagram of elements that are equipped in or mounted in a housing of the apparatus 100 of FIG. 1A. The apparatus 100 for biometric information detection according to the exemplary embodiment may be mounted in a wearable device that a user can put on, or may be configured to be a part of the wearable device. The wearable device may include devices of a wristwatch type, a bracelet type, a wristband type, a ring-type, a hairband type, a body belt type, a neck band type, etc., and may not be limited to any shape or size. Referring to FIGS. 1A and 1B, the apparatus 100 includes a housing 110, a biometric sensor 120, an impedance measurer 130, and a processor 140. The biometric sensor 120, the impedance measurer 130, and the processor 140 are mounted or built in the housing 110. Some of the elements mounted in the housing 110 may be exposed to the outside of the housing 110, or may protrude from the housing 110.

The shape, size, and thickness of the housing 110 are not particularly limited. For example, the housing 110 may be made of a relatively rigid material, such as plastic or metal, or a flexible material. The housing 110 may include at least one surface 112 that is entirely or partially flat. The surface 112 is a contact surface with a target subject. As will be described later, the apparatus 100 includes a plurality of biometric electrode pairs 132 and the biometric sensor 120 on the surface 112, and detects biometric information and measures bio-impedances through the surface 112.

The biometric sensor 120 is a sensor that can directly or indirectly measure the biometric information of the target subject. The biometric information may be various types of information of a living organism, such as a human being, wherein the information may be a pulse wave, blood glucose, heartbeat, breathing, stress, calorie expenditure, calorie intake, etc. The biometric sensor 120 may directly measure and obtain the biometric information through the surface 112 of the housing 110. Alternatively, the biometric sensor 120 may receive a predetermined measurement signal through the surface 112 of the housing 110 and apply a predetermined correlation model to the measurement signal to obtain or estimate the biometric information. To this end, the biometric sensor 120 may be constructed to allow a biometric signal measurement device or a measurement signal receiver to be directly or indirectly exposed to the surface 112 of the housing 110. Also, the correlation model may be updated using data obtained and/or estimated, i.e., the detected biometric information.

Direct detection of the biometric information or estimation of the biometric information using the measurement signal may be independently implemented through hardware or software built in the housing 110, or may be implemented as a function of the processor 140. In this case, the estimation of the biometric information may be carried out by a biometric information estimation apparatus other than by the apparatus 100 for biometric information detection, in which case the apparatus 100 may include a communicator to transmit the measurement signal to the biometric information estimation apparatus.

The biometric sensor 120 may detect biometric information or measure a biometric signal of the target subject according to a predetermined control signal. The control signal is generated by a controller that controls the operation of the apparatus 100 and is transmitted to the biometric sensor 120. The controller is implemented as a function of the processor 140, which will be described below, but the aspects of the present disclosure are not limited thereto.

In addition, the biometric sensor 120 may measure the biometric information or the biometric signal of the target subject in a physical or chemical manner, which is not particularly limited. For example, the biometric sensor 120 may include an optical signal detector to irradiate light onto the target subject according to a predetermined control signal and receive light returning from the target object. Also, the biometric sensor 120 may analyze the optical signal received by the optical signal detector using an algorithm to estimate biometric information. In this case, according to a type of the biometric sensor 120, the biometric sensor 120 may obtain spectral data by scattering the light returning from the target subject or estimate biometric information by analyzing the received spectrum. In this case, direct detection of infrared biometric information using near infrared ray (NIR) or mid-infrared ray (MIR) or estimation of biometric information using a measurement signal may be separately implemented by hardware or software that is mounted in the housing 110, or these operations may be implemented as functions of the processor 140, which will be described below. At this time, infrared spectroscopy that uses NIR, MIR or Raman spectroscopy may be used.

The biometric sensor 120 may perform measurement while facing the target subject in a predetermined direction. For example, the biometric sensor 120 measures the biometric information while facing and being parallel to one surface of the target subject and, according to a type of the biometric sensor 120, the biometric sensor 120 may measure the biometric information while being in direct contact with the target subject or while being apart from the target object at a distance. The contact or spacing between the biometric sensor 120 and the target subject may be previously limited according to the structure or position at which the biometric sensor 120 is installed on the surface 112 of the housing 110. If the biometric sensor 120 is in direct contact with the target subject, a state of the biometric sensor 120 opposed to the target subject, that is, a state of contact may be represented as a distribution of local pressures exerted on the biometric sensor 120 by the target subject.

If the biometric sensor 120 facing the target subject is not in an appropriate state, measurement may not be performed accurately. For example, depending on a type of the biometric sensor 120, changes in the state in which the biometric sensor 120 is opposed to the target subject (hereinafter, will be referred to as a "facing state") may cause changes in measured values, and hence the validity of the measured values may be significantly degraded. If the biometric sensor 120 is an optical sensor, a slight change in the facing state may cause noise in a measurement signal, and thus it may be helpful to ensure an accurate facing state at the time of measurement or to maintain a stable facing state for a long period of time.

Figure 2:
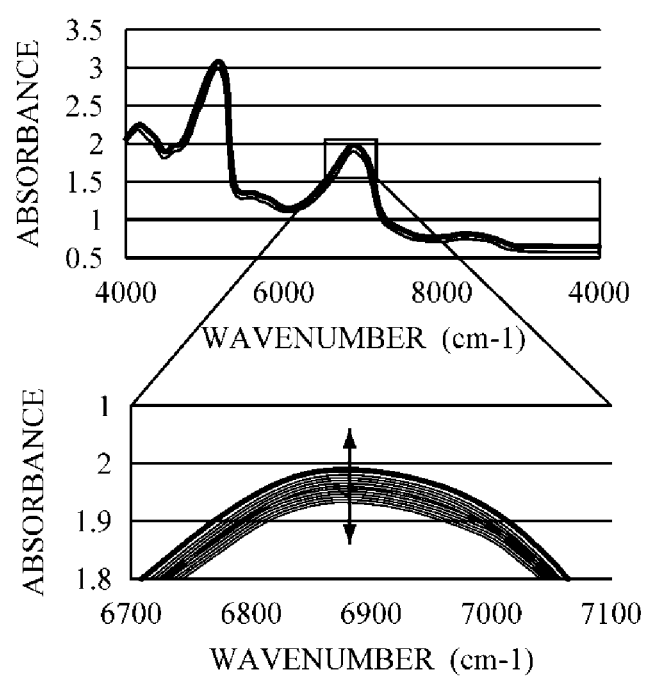
FIG. 2 illustrates graphs of skin spectra of a user that are measured using a Fourier transform infrared ray (FT-IR) spectrometric sensor.

FIG. 2 illustrates graphs of skin spectra of a user that are measured using a Fourier transform infrared ray (FT-IR) spectrometric sensor. The skin spectra shown in FIG. 2 are measured several tens of times by the FT-IR spectrometric sensor that is fixed in tight contact with the wrist of the user. Referring to FIG. 2, although the FT-IR spectrometric sensor is fixed onto the wrist, the measured spectra contain noise so that most wavenumbers are different in the absorbance. This indicates that the facing state or contact state relative to the skin has slightly changed over time and, accordingly, the measured values can vary.

Referring again to FIGS. 1A and 1B, the impedance measurer 130 includes a plurality of, i.e., two or more biometric electrode pairs 132 that are disposed around the biometric sensor 120. The plurality of biometric electrode pairs 132 are formed on the surface 112 of the housing 110. In FIG. 1A, it is illustrated that two biometric electrode pairs 132a and 132b are arranged along a first direction $X_{11}$ and a second direction $X_{12}$, respectively, such that electrodes in each pair are arranged symmetrically with respect to the biometric sensor 120, but such arrangement is only an example. Examples of arrangement of a plurality of biometric electrode pairs 132 around the biometric sensor 120 will be described later.

The surface areas of biometric electrodes in each pair 132 may be the same as each other. In this case, when the surface areas of the biometric electrodes are the same as each other, it does not indicate the physical sameness only, but may also include the case in which there are slight differences in the contacting surface areas as long as the magnitude of bio-impedance to be measured is not affected. Therefore, a definition of sameness of the surface areas between the biometric electrodes may vary depending on a type of bio-impedance to be measured.

The biometric electrodes in each pair 132 may also protrude from the surface 112 of the housing 110 to reach the same height. The biometric electrodes 132a and 132b protruding from the surface 112 may include the case in which the biometric electrodes 132a and 132b are embedded in such a way that their surfaces are in parallel to the surface 112 of the housing 110, in other words the height of the biometric electrodes 132a and 132b from the surface 112 of the housing 110 is 0. Heights of the protruding biometric electrodes may vary according to a type of bio-impedance to be measured or an operating method or structure of the biometric sensor 120 (e.g., a height of the biometric sensor 120 protruding from the surface 112, etc.). For example, the heights of the protruding biometric electrodes 132a and 132b may be the same as or greater than the height of the protruding biometric sensor 120.

The impedance measurer 130 measures bio-impedances through each of the biometric electrode pairs 132. The impedance measurer 130 may measure a bio-impedance on a local area of the target subject, for which the bio-impedance of the target subject is measured along a path between the two biometric electrodes 132a or 132b in either pair 132. In the case of FIG. 1A, the bio-impedance of a local area of the target subject is measured in the first direction $X_{11}$ and the second direction $X_{12}$. The type of bio-impedance that the impedance measurer 130 can measure is not particularly limited. For example, the impedance measurer 130 may measure a variety of bio-impedances, such as a phase angle, a resistance that indicates the relative amount of muscle and fat, total body water, a moisture percentage, fat mass, body mass index, etc.

To this end, the impedance measurer 130 includes a voltage applying apparatus to apply a predetermined voltage to the biometric electrode pairs 132, and an impedance measurement apparatus. However, the configuration of the impedance measurer 130 is not particularly limited. For example, the configuration of a bio-impedance meter that is currently widely used in the art, as well as the configuration of a bio-impedance meter that will be used in the future may be included in the impedance measurer 130.

The processor 140 calculates a bio-impedance ratio, which is a ratio between bio-impedances measured by the impedance measurer 130. The "bio-impedance ratio" refers to a ratio of bio-impedance measured using one biometric electrode pair to bio-impedance measured using another biometric electrode pair. For example, the processor 140 may calculate a ratio of a second bio-impedance measured through a second biometric electrode pair 132b to a first bio-impedance measured through a first biometric electrode pair 132a. In this case, the first biometric electrode pair 132a may be a reference electrode pair and the second biometric electrode pair 132b is a measurement electrode pair. The reference electrode pair and the measurement electrode pair may be arbitrarily determined or the reference electrode pair may be determined according to a predetermined criterion (e.g., a characteristic of a surface shape of a measurement area of the target subject, etc.).

To this end, the processor 140 receives a plurality of measured bio-impedance values from the impedance measurer 130. Then, the processor 140 calculates a ratio between two bio-impedance values among the received bio-impedance values. If there are three or more biometric electrode pairs 132, the processor 140 may determine a reference bio-impedance value measured using one of the biometric electrode pairs 132 and calculate the bio-impedance ratios between the reference bio-impedance value and the bio-impedance values measured using each of the remaining biometric electrode pairs 132. In this case, the biometric electrode pair that is used to measure the reference bio-impedance value may be a reference electrode pair and the reaming biometric electrode pairs may be measurement electrode pairs.

The processor 140 determines the validity of the biometric information detected by the biometric sensor 120 based on the calculated bio-impedance ratio. For example, the processor 140 may determine that the biometric information measured by the biometric sensor 140 is valid if the calculated bio-impedance ratio falls within a predetermined range. Alternatively, when a sequential change in the calculated bio-impedance ratio reaches a predetermined range or said ratio becomes constant, the processor 140 may determine that only the biometric information that has been measured since that time is valid. Hereinafter, the above examples will be described in more detail.

The magnitude of bio-impedance may change according to the state of skin, fat, muscle, and water of the target subject so that it may vary depending on where it is measured or when it is measured. On the contrary, if the bio-impedance with respect to the same local area of the target subject is measured simultaneously or at almost the same time, the magnitude of the bio-impedance is substantially the same, no matter where they are measured. The same area to be measured does not necessarily mean that the areas of the biometric electrode pairs may overlap or the measurement paths overlap or intersect with each other, and as long as each measurement path belongs to the local area to the extent that can be considered as being the same area by those skilled in the art, it can be assumed that the measurement areas are the same. For example, in FIG. 1A, the area of the target subject in contact with the surface 112 of the housing, in other words, the area of the target subject with a size that corresponds to the area of the surface 112 of the housing 110 can be assumed as the same area.

When the magnitudes of the bio-impedances measured on the same local area are equal to each other, regardless of the measurement path or the measurement direction, it is based on the premise that the contact state of each biometric electrode to the target subject is the same. For example, when a biometric electrode pair is in full contact with the target subject, the medium on the measurement path may be composed of biometric components of the target subject only, whereas when in partial contact with the target subject, the medium on the measurement path also contains air, as well as the biometric components. In addition, according to the extent in which the biometric electrode pair is in partial contact with or spaced apart from the target subject, the ratio of the biometric components and the air in the medium varies. As a result, the contact state of the biometric electrode pair to the target subject varies, and thus even when the same local area is measured, the medium components on the same measurement path are changed so that the magnitude of a bio-impedance measured also varies.

Therefore, when the bio-impedance ratio of the biometric electrode pairs is known, the contact state between each of the biometric electrode pairs and the target subject can be identified. More precisely, a difference in a contact state between the reference electrode pair and the measurement electrode pair can be identified based on the bio-impedance ratio. In addition, if one of the biometric electrode pairs can be in entire contact with the target subject, a bio-impedance ratio can be measured by designating the contacting biometric electrode pair as a reference, and based on the bio-impedance ratio, the contact states of the measurement electrode pairs can be identified.

In addition, if the sequential change in the bio-impedance ratio is known, it is possible to identify whether a relative contact state between each biometric electrode pair and the target subject is maintained the same or varies over time. In case the biometric electrode pair that does not change in the contact state over time is set as a reference biometric electrode pair, it is possible to identify whether the contact state of each measurement electrode pair is varied or not.

As illustrated in FIG. 1A, the biometric electrode pairs 132a and 132b are distributed around the biometric sensor 120. In addition, the biometric electrode pairs 132a and 132b and the biometric sensor 120 are disposed close to each other on the surface 112 of the housing 110 that has a small area. Thus, a relative state of contact between each of the biometric electrode pairs 132a and 132b and the target subject, which is represented as a bio-impedance ratio, or the sequential change thereof is closely associated with a state of contact or a state of facing between the biometric sensor 120 and the target subject or the sequential change thereof.

For example, if the value of a bio-impedance ratio measured using the biometric electrode pairs 132a and 132b is known, a facing state or a contact state of the biometric sensor 120 with respect to the target subject can be identified from the direction in which each biometric electrode pair 132a and 132b is aligned. For example, if the biometric electrode pairs 132a and 132b are disposed as shown in FIG. 1A, by using the bio-impedance ratio, it is possible to identify whether the biometric sensor 120 is opposed and parallel to or makes contact with the target subject in the first direction $X_{11}$ or the second direction $X_{12}$, or whether the biometric sensor 120 is opposed to or makes contact with the target subject in a slanted manner in the first direction $X_{11}$ or the second direction $X_{12}$. When it is ensured that the biometric sensor 120 is opposed and parallel to the target subject in the first direction $X_{11}$ and the contact state to the target subject is not varied, by using the bio-impedance ratio, it is possible to identify whether the biometric sensor 120 is opposed and parallel to the target subject in the second direction $X_{12}$ or is opposed in a slanted manner to the target subject in the second direction $X_{12}$.

In addition, if the sequential change in the bio-impedance ratio measured using the biometric electrode pairs 132a and 132b is known, it is possible to know whether the facing state or the contact state of the biometric sensor 120 with respect to the target subject is maintained constant or there is a change in said state. For example, if the biometric electrode pairs 132a and 132b are disposed as shown in FIG. 1A, by using the sequential change in the bio-impedance ratio, it is possible to identify whether the facing state of the biometric sensor 120 with respect to the target subject is maintained constant or the facing state has changed in the first direction $X_{11}$ or the second direction $X_{12}$. When it is ensured that the biometric sensor 120 and the target subject are constantly opposed and parallel to each other in the first direction $X_{11}$, by using the bio-impedance ratio, it is possible to detect whether the biometric sensor 120 is maintained to be constantly opposed to the target subject in the second direction $X_{12}$ or there is a change in the facing state.

According to the above-described principles, the processor 140 determines whether the biometric information or biometric signal measured by the biometric sensor is valid based on the calculated bio-impedance ratio value. For example, if the bio-impedance ratio falls within a predetermined range, it can be construed that the conditions for the facing state of the biometric sensor 120 with respect to the target subject are satisfied, and the processor 140 may determine that the detected biometric information is valid. For example, if the ratio is "1" or close to "1," it can be construed that the biometric sensor 120 is opposed and parallel to the target subject, and the processor 140 may determine that the detected biometric information is valid. If the biometric sensor 120 estimates the biometric information from a measured biometric signal by applying a predetermined correlation model, the correlation model may be updated using valid data only.

The processor 140 may determine whether the biometric information or biometric signal detected by the biometric sensor 120 is valid, based on the changes in the calculated bio-impedance ratio over time. For example, if there is no sequential change in the bio-impedance ratio or the sequential change falls within a predetermined range, it can be construed that the facing state of the biometric sensor 120 with respect to the target subject is stable, and the processor 140 may determine that only the biometric information that is detected after a time point is valid. If the biometric sensor 120 estimates the biometric information from a measured biometric signal by applying a predetermined correlation model, the biometric sensor 120 may update the correlation model by using valid data only.

As described above, the bio-impedance ratio between the biometric electrode pairs of biometric electrodes arranged at different locations and/or in different directions around the biometric sensor shows the facing state or contact state of the biometric sensor with respect to the target subject. And the sequential change in the bio-impedance ratio shows whether said facing state or contact state changes or is maintained over time.

Figure 3A:
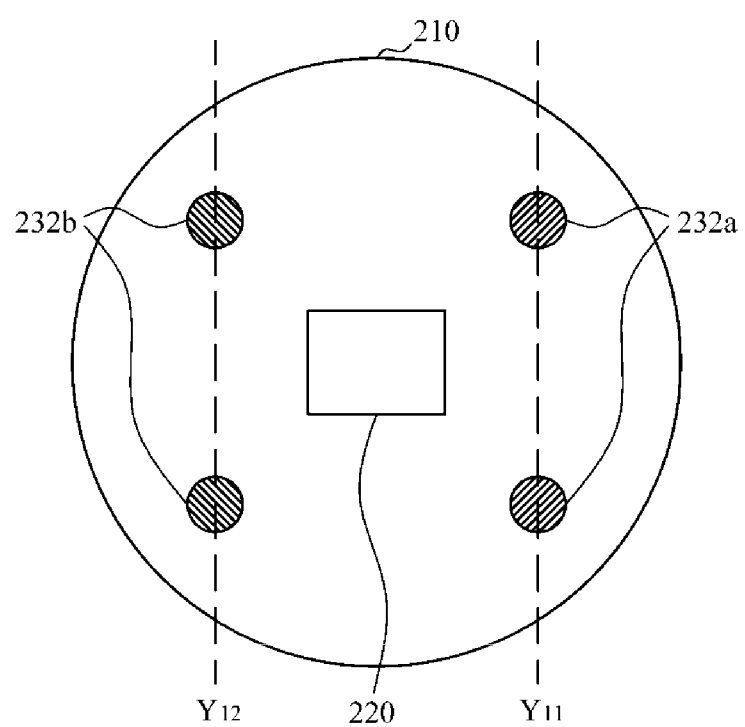
FIG. 3A is a diagram illustrating a plurality of biometric electrode pairs arranged in an apparatus for biometric information detection, according to an exemplary embodiment.

FIG. 3A is a diagram illustrating a plurality of biometric electrode pairs arranged in an apparatus for biometric information detection, according to an exemplary embodiment. Unlike FIG. 1A, FIG. 3A depicts that a housing 210 of the apparatus for biometric information detection is circular-shaped, which is only an example. Also, FIG. 3A depicts one reference electrode pair 232a and one measurement electrode pair 232b, which are also an example. As described above, there may be one or more measurement electrode pairs 232b.

Referring to FIG. 3A, the two biometric electrodes of the reference electrode pair 232a are all arranged to the right of a biometric sensor 220 along a direction $Y_{11}$, and the two biometric electrodes of the measurement electrode pair 232b are all arranged to the left of the biometric sensor 220 along a direction $Y_{12}$. The directions $Y_{11}$ and $Y_{12}$ may be parallel to each other, which is also an example. In addition, in the example shown in FIG. 3A, the reference electrode pair 232a and the measurement electrode pair 232b may be changed to each other. According to exemplary embodiments, rather than disposing the biometric electrode pairs 232a and 232b as shown in FIG. 3A, the biometric electrode pairs may be disposed above and below the biometric sensor 220, or other biometric electrode pairs may be further disposed above and below the biometric sensor 220, respectively, in addition to the biometric electrode pairs 232a and 232b shown in FIG. 3A.

In the example shown in FIG. 3A, based on a bio-impedance ratio of the measurement electrode pair 232b to the reference electrode pair 232a, it is possible to identify whether the biometric sensor 220 is opposed and parallel to, or is opposed in a slanted manner to, the target subject in a direction perpendicular to either the left or right direction, i.e., direction $Y_{11}$ or $Y_{12}$. For example, if the bio-impedance ratio is 1 or within a range including 1, it may be identified that the biometric sensor 220 is opposed and parallel to the target subject in the left or right direction. Alternatively, if a change in bio-impedance reaches a predetermined range after a time point, it may be viewed that the biometric sensor 220 is maintained to be opposed and parallel to the target subject in a left or right direction from the time point.

According to another exemplary embodiment, the two biometric electrodes in the reference electrode pair may be disposed symmetrically to each other with respect to the biometric sensor, and an example is as shown in FIG. 1A (refer to the biometric electrode pair 132a). As shown in FIG. 1A, if direction $X_{11}$ in which the reference electrode pair 132a and direction $X_{12}$ in which the measurement electrode pair 132b are perpendicular to each other, it is possible to determine whether the biometric sensor is opposed and parallel to the biometric sensor 120 in a left-and-right or up-and-down direction with respect to the target subject, or whether the biometric sensor is opposed in a slanted manner to the target subject in a left-and-right or up-and-down direction, by using only the two biometric electrode pairs.

Figure 3B:
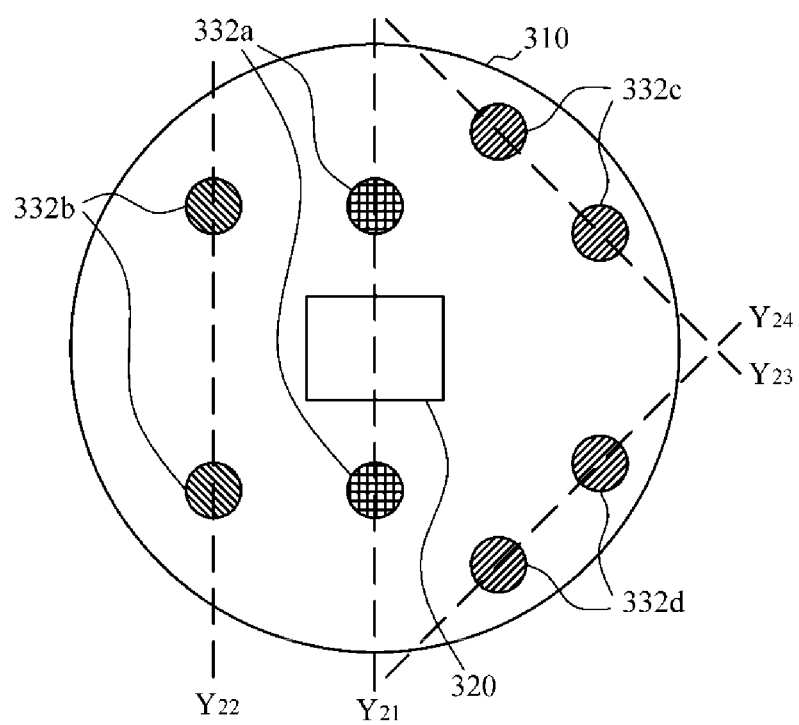
FIG. 3B is a diagram illustrating a plurality of biometric electrode pairs arranged in an apparatus for biometric information detection, according to another exemplary embodiment.

FIG. 3B is a diagram illustrating a plurality of biometric electrode pairs arranged in an apparatus for biometric information detection, according to another exemplary embodiment. In FIG. 3B, a housing 310 includes one reference electrode pair 332a and three measurement electrode pairs 332b, 332c, and 332d, and these are only an example.

Referring to FIG. 3B, biometric electrodes of the reference electrode pair 332a are disposed symmetrically to each other in a vertical direction $Y_{21}$ with respect to a biometric sensor 320. In addition, two biometric electrodes of a first measurement electrode pair 332b are all disposed to the left of the biometric sensor 320 along a vertical direction $Y_{22}$. Direction $Y_{22}$ is not necessarily parallel to direction $Y_{21}$. In this case, based on a bio-impedance ratio of the first measurement electrode pair 332b to the reference electrode pair 332a, it is identified whether the biometric sensor 320 is opposed and parallel to the target subject or is opposed in a slanted manner to the target subject in a direction perpendicular to the left direction, i.e., direction $Y_{22}$.

Two biometric electrodes of a second measurement electrode pair 332c are all disposed to the right of the biometric sensor 320 in a direction $Y_{23}$, and two biometric electrodes of a third measurement electrode pair 332d are all disposed to the lower right of the biometric sensor 320 in a direction $Y_{24}$. Direction $Y_{23}$ is not necessarily perpendicular to direction $Y_{24}$, and the second measurement electrode pair 332c and the third measurement electrode pair 332d are not necessarily all equipped simultaneously in the apparatus for biometric information detection. In this case, based on bio-impedance ratios of each of the second and third measurement electrode pairs 332c and 332d to the reference electrode pair 332a, it is identified whether the biometric sensor 320 is opposed and parallel to the target subject or is opposed in a slanted manner to the target subject in a upper-right direction or in a lower-right direction.

Figure 3C:
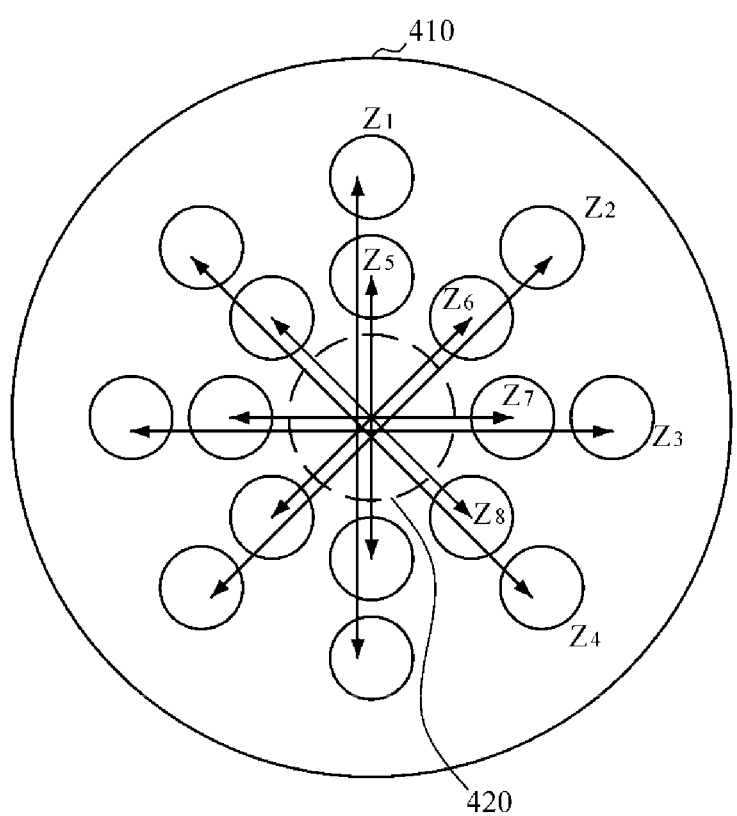
FIG. 3C is a diagram illustrating a plurality of biometric electrode pairs arranged in an apparatus for biometric information detection, according to another exemplary embodiment.

FIG. 3C is a diagram illustrating a plurality of biometric electrode pairs are arranged in an apparatus for biometric information detection, according to another exemplary embodiment. In FIG. 3C, eight biometric electrode pairs Z1 to Z8 are disposed symmetrically to each other on one surface of a housing 410, in which one of the eight biometric electrode pairs Z1 to Z8 may be a reference electrode pair and the remaining seven electrode pairs may be measurement electrode pairs. In this case, it is apparent that up to seven bio-impedance ratios can be obtained.

Referring to FIG. 3C, the total of eight biometric electrode pairs Z1 to Z8 are all disposed symmetrically to each other with respect to a biometric sensor 420. The adjacent biometric electrode pairs are evenly arranged in four directions at intervals of 45 degrees to each other around the biometric sensor 420. By doing so, based on each bio-impedance ratio, it is identified whether the biometric sensor 420 is opposed and parallel to the target subject or is opposed in a slanted manner to the target subject in orthogonal directions (refer to biometric electrode Z2 and Z4 as well as in a left-and-right direction and a up-and-down direction (refer to biometric electrode pairs Z1 and Z3). Consequently, as compared to the example shown in FIG. 1A, the accuracy in detecting the slanted direction of the biometric sensor 420 can be more enhanced. In addition, in FIG. 3C, two biometric electrode pairs (e.g., Z3 and Z7) that have different distances between their electrodes are arranged in each direction, thereby allowing more accurate detection of opposed facing state, i.e., a degree of slant, of the biometric sensor in the direction.

Figure 4:
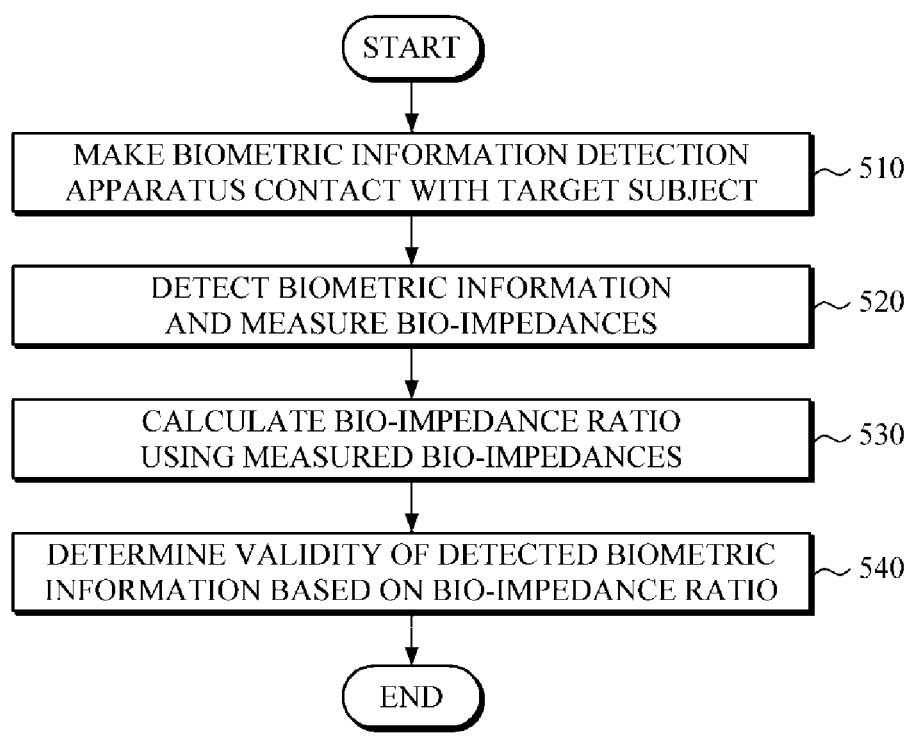
FIG. 4 is a flowchart illustrating a method of biometric information detection, according to an exemplary embodiment.

FIG. 4 is a flowchart illustrating a method of biometric information detection, according to an exemplary embodiment. The method shown in FIG. 4 may be performed by the apparatus for biometric information detection illustrated in FIGS. 1A and 1B. Thus, to avoid redundancy, the method of biometric information detection will be described briefly.

Referring to FIGS. 1A and 4, the apparatus 100 for biometric information detection is adhered to the target subject such that one surface 112 of the housing 110 of the apparatus 100 in which the biometric sensor 120 and the plurality of biometric electrode pairs 132 are disposed makes close contact with the target subject, as depicted in 510. The apparatus 100 may be mounted in a wearable device. In this case, an area of the target subject to which the apparatus 100 is adhered is not particularly limited, and may include a wrist, an ankle, an arm, a leg, etc.

Then, biometric information of the target subject is detected using the biometric sensor, and bio-impedances are measured using the plurality of biometric electrode pairs 132, as depicted in 520. The procedure for detecting the biometric information and the procedure for measuring the bio-impedance may be performed simultaneously. However, they are not necessarily performed at the same time physically, and even a slight difference in time would be acceptable, as long as the two procedures can be regarded as being performed simultaneously.

Then, a bio-impedance ratio is calculated using the measured bio-impedances, as depicted in 530. As described above, the bio-impedance ratio may be a ratio of bio-impedance measured using each of one or more measurement electrode pairs to bio-impedance measured using a reference electrode pair.

Subsequently, the validity of the biometric information detected in 520 is determined based on the bio-impedance ratio calculated in 530, as depicted in 540. For example, the bio-impedance ratio falls within a predetermined range, it may be determined that the biometric information is valid. Alternatively, in the case in which it is considered that the change in the bio-impedance ratio reaches a predetermined range at a time point and thereafter remains substantially constant, it may be determined that only the biometric information that has been detected because the time point is valid. According to exemplary embodiments, data training on an algorithm that represents a correlation for biometric information estimation may be performed by using measurement data of the valid biometric information.

Figure 5A:
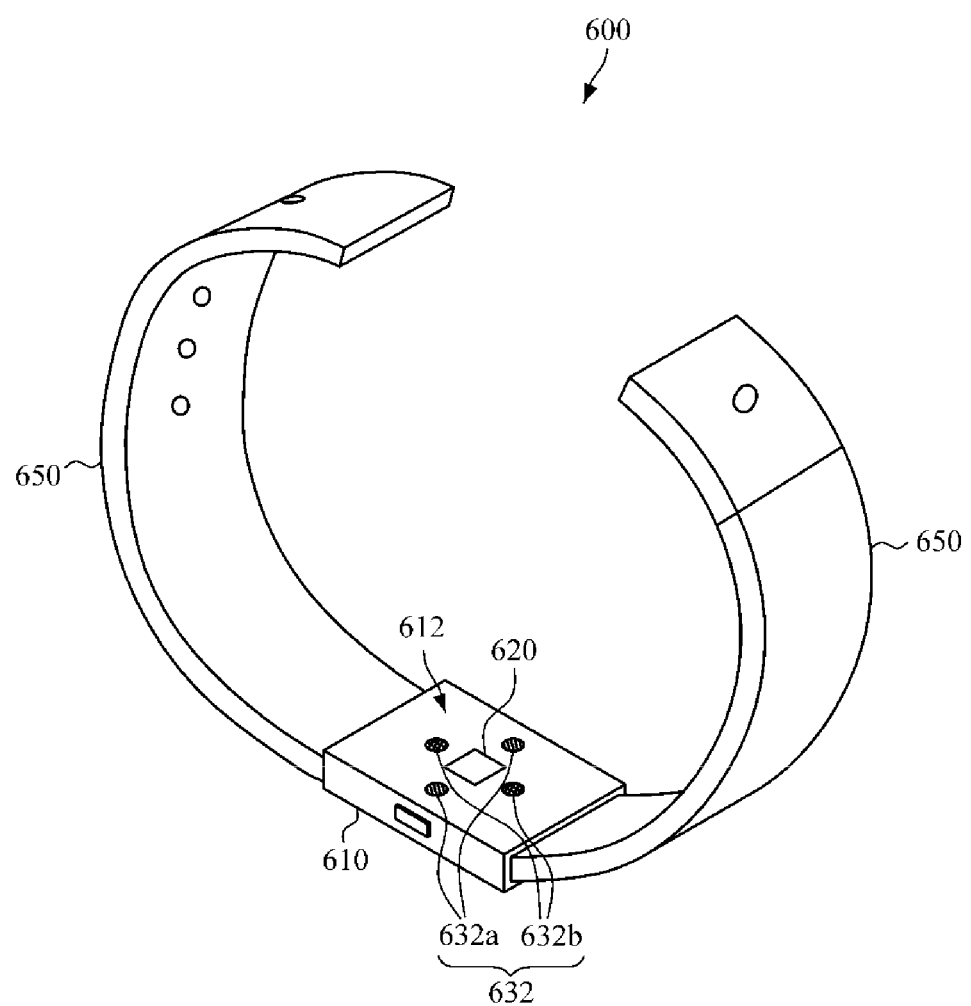
FIG. 5A is a perspective view of a wearable device according to an exemplary embodiment.
Figure 5B:
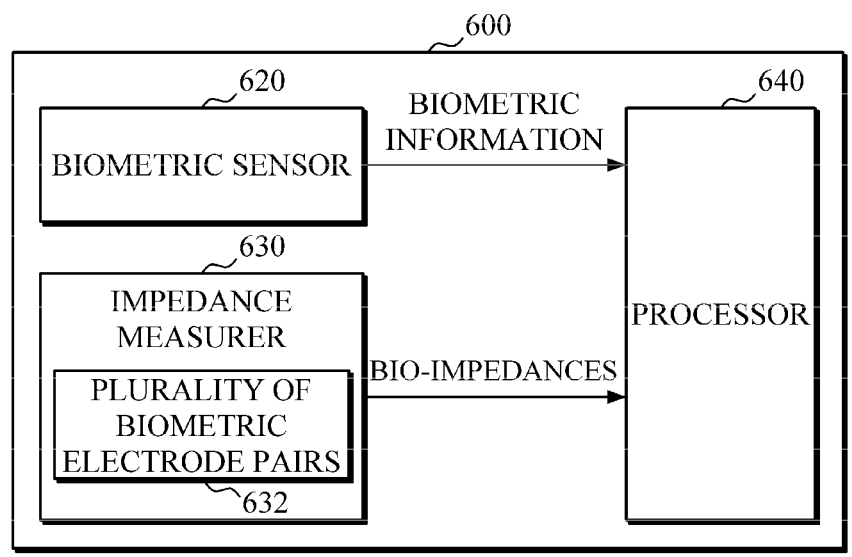
FIG. 5B is a block diagram illustrating elements mounted in the wearable device of FIG. 5A.

FIG. 5A is a perspective view of a wearable device 600 according to an exemplary embodiment. FIG. 5B is a block diagram illustrating elements mounted in the wearable device 600 of FIG. 5A. Exemplary embodiments of the apparatus for biometric information detection described above may be mounted in a smart band-type wearable device that can be put on the user's wrist. However, this is only an example for the convenience of description. The wearable device may be implemented in various types, such as a wristwatch type, a bracelet type, a ring-type, a hairband type, a body belt type, a neck band type, etc. In addition, FIGS. 5A and 5B illustrate that the wearable device has the apparatus 100 for biometric information detection shown in FIGS. 1A and 1B mounted therein, which is only example.

Referring to FIGS. 5A and 5B, the wearable device 600 includes a housing 610, a biometric sensor 620 disposed on a surface 612 of the housing 610, an impedance measurer 630 that includes a plurality of biometric electrode pairs including a first biometric electrode pair 632a and a second biometric electrode pair 632b disposed on the surface 612, a processor 640, and a wearing member 650. The configuration of the wearable device 600 is different from the apparatus 100 illustrated in FIGS. 1A and 1B in that the wearable device 600 further includes the wearing member 650. Hereinafter, the wearable device 600 will be described with focus on the differences from the apparatus 100 described with reference to FIGS. 1A and 1B. Therefore, what is describe with respect to the apparatus 100 can apply to any details of the wearable device 600 that are not specifically described herein, unless otherwise explicitly stated to be excluded.

A battery may be mounted in the housing 610 or the wearing member 650 to supply power to the wearable device 600. The battery may be a rechargeable battery, and the housing 610 or the wearing member 650 may include a port to recharge the battery. In addition, a display of a size may be provided on the other surface of the housing 610, i.e., the opposite surface of the surface 312. The display may be a touch screen. In addition to the touch screen, the housing 610 may further include various types of input interfaces and output interfaces (e.g., an audio output interface) for interaction with a user. Furthermore, the housing 610 may also include a communicator to communicate with other external devices.

The wearing member 650 is connected to each side of the housing 610 and extends in one direction. The wearing member 650 may be a strap designed to encircle the user's body part, for example, the wrist. To this end, the wearing member 650 may be completely or partially made of a flexible material. For example, the wearing member 650 may be adapted to encircle a body part of the user or adapted to be separated from the body part.

In order for the user to wear the wearable device 600 of FIG. 5A, the wearing member 650 may be used in a manner that the user wraps the wearing member 650 around the user's wrist. The user uses the wearing member 650 to wear the wearable device 600 in a manner that the wearing member 650 encircles a user's body part, for example, a wrist, an ankle, a finger, a torso, an arm, a leg, a neck, etc. Although there is a difference in degree from person to person, the body part on which the wearable device 650 is worn is flat in the longitudinal direction. On the contrary, the direction perpendicular to the longitudinal directions the direction in which the wearing member 650 extends and encircles the body part. The body part around that the wearing member 650 is wrapped tends to have a central portion higher than the edge portions, although there is a difference in degree depending on the body part. For example, the surface of the wrist in the longitudinal direction of the arm is flat, while the central portion of the surface in a direction perpendicular to the longitudinal direction is convex or the surface is curved toward the edges.

Among the plurality of biometric electrode pairs 632 included in the wearable device 600, the first biometric electrode pair 632a aligned in a first direction may be set as a reference electrode pair, and the second biometric electrode pair 632b aligned in a second direction may be set as a measurement electrode pair, to use the structural features of the body part on which the wearable device 600 is put. By doing so, when the user wears the wearable device 600, the reference electrode pair 632a aligned in a longitudinal direction of the body part is always in close contact with the wrist. As a result, it is ensured that the biometric sensor 620 is opposed and parallel to the wrist's skin in the longitudinal direction of the arm. On the contrary, the measurement electrode pair 632b aligned along a direction perpendicular to the longitudinal direction of the body part on which the wearable device 600 is put, in other words a direction in which the wearing member 650 extends, may not properly contact the wrist or, in worse cases, it is taken off from the wrist, and many changes in the contact state may occur over time. Consequently, the biometric sensor 620 may be attached in a slanted manner to the wrist in the direction perpendicular to the longitudinal direction of the arm or changes in the facing state may be liable to occur over time.

Therefore, when the calculated bio-impedance ratio is close to "1" or lies within a predetermined range, the processor 640 may determine that the biometric information detected by the biometric sensor 620 is valid. Alternatively, when the calculated bio-impedance ratio is within a predetermined range and the sequential change thereof is maintained almost constant, the processor 640 may determine that the biometric information detected by the biometric sensor 620 is valid.

In addition, based on the calculated bio-impedance ratio, the processor 640 may generate information. For example, the processor 640 may generate not only information indicating the validity of the detected biometric information, but also information to request to re-conduct the measurement when the biometric information is invalid. In addition, the processor 640 may not only generate information indicating the state in which the wearing device 600 is worn, but also generate information for guiding the wearing, thereby enabling the user to correct the state of wearing the wearable device 600. Also, the information generated by the processor 640 may be output through the display or the audio output interface or may be transmitted to another electronic device via the communicator.

Figure 6A:
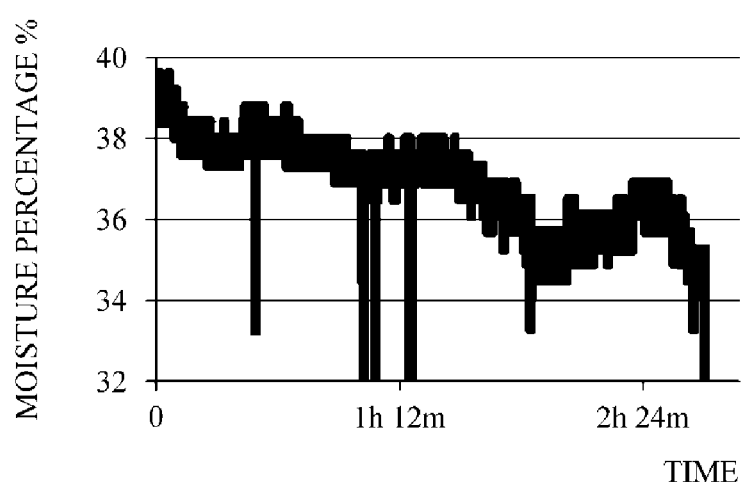
FIG. 6A is a graph showing a variation in bio-impedance over time for which a bio-impedance is measured using a first biometric electrode pair while a user is wearing the wearable device of FIG. 5A on a wrist.
Figure 6B:
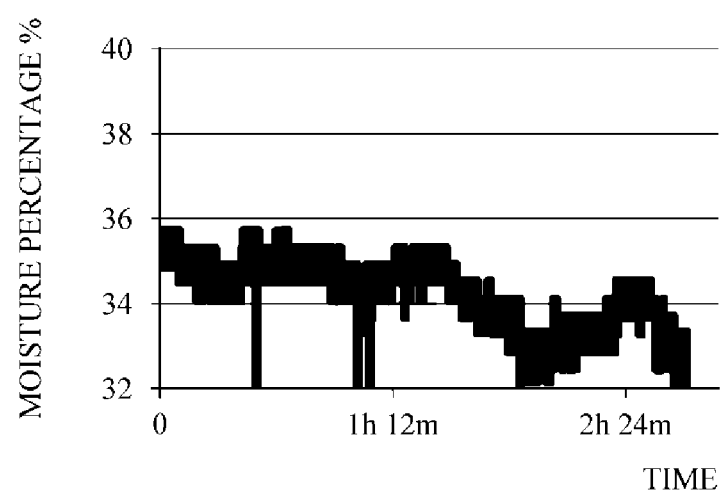
FIG. 6B is a graph showing a variation in bio-impedance over time for which a bio-impedance is measured using a second biometric electrode pair while the user is wearing the wearable device of FIG. 5A on the wrist.

FIG. 6A is a graph showing a variation in bio-impedance over time for which a bio-impedance is measured using the first biometric electrode pair 632a while a user is wearing the wearable device 600 of FIG. 5A on a wrist. FIG. 6B is a graph showing a variation in bio-impedance over time for which a bio-impedance is measured using the second biometric electrode pair 632b while the user is wearing the wearable device 600 of FIG. 5A on the wrist. The bio-impedance shown in FIG. 6A is measured using the first biometric electrode pair 632a, and the bio-impedance shown in FIG. 6B is measured using the second biometric electrode pair 632b. FIGS. 6A and 6B show an example in which a moisture percentage as the bio-impedance is measured for a length of time (2 hours and 24 minutes). In this example, the user does not take any further water or excretes water in the form of sweat or the like during the time of the measurement.

Referring to FIGS. 6A and 6B, it is viewed that the moisture percentages measured using the first biometric electrode pair 632a and the second biometric electrode pair 632b are all reduced by about 15 to 20% over time. This shows that the moisture in the skin decreases as time elapses. In addition, referring to FIGS. 6A and 6B, it is shown that absolute values of the moisture percentages measured are different between the first biometric electrode pair 362a and the second biometric electrode pair 362b, and this can be assumed to be due to the fact that the second biometric electrode pair 632b makes less contact with the skin than the first biometric electrode 632a.

Figure 6C:
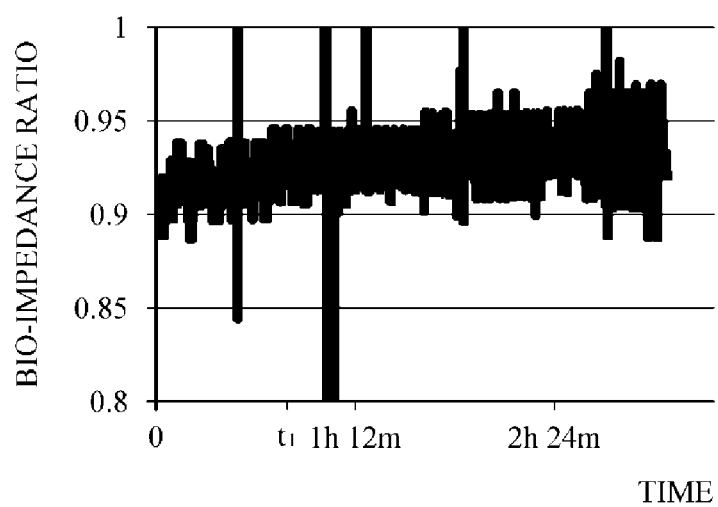
FIG. 6C is a graph showing a variation in a bio-impedance ratio that is obtained using the measured bio-impedances shown in FIGS. 6A and 6B.

FIG. 6C is a graph showing a variation in a bio-impedance ratio that is obtained using the measured bio-impedances shown in FIGS. 6A and 6B. Referring to FIG. 6C, except some time points at which errors occur in the measures shown in FIGS. 6A and 6B, the bio-impedance ratio appears overall greater than 0.9 and is maintained constant around 0.93. Although the criteria of the processor 640 for determining the validity of the biometric information detected may vary depending on the type of biometric information detected, the wearing position, or a type of the biometric sensor 630, all the biometric information detected during the pertinent time period may be assumed to be valid, if the bio-impedance ratio lies within the range as shown in FIG. 6C. In another example, because the bio-impedance ratio becomes more constant after time $t_1$, it may be determined that only the biometric information detected since that time $t_1$ is valid.

Because the bio-impedance ratio calculated in a state in which the biometric electrode pair 632a aligned in a longitudinal direction of the user's body part on which the wearable device 600 is put serves as a reference electrode pair and the biometric electrode pair 632b aligned in a direction in which the wearing member 650 extends serves as a measurement electrode pair is closely related to the state of the user wearing the wearable device 600, the bio-impedance ratio of the wearable device 600 that is calculated by the processor 640 can be regarded as a fitting index. For example, a greater bio-impedance ratio, i.e., a greater fitting index may indicate that the user is wearing the wearable device in closer contact with the user's body part by tightening the wearing member 650. Accordingly, based on the calculated bio-impedance ratio, i.e., the fitting index, the processor 640 may be able to determine a state of the user wearing the wearable device 600, for example, whether the user is wearing the wearable device 600 properly or too tightly or loosely using the wearing member 650 tightened around the wrist and based on a result of the determination, the processor 640 may generate information for guiding the wearing to guide the user to correct the state of the user wearing the wearable device 600. The generated guiding information may be output for the user through an output interface of the wearable device 600, such as a touch screen or a speaker. According to exemplary embodiments, the processor 640 may also generate the result of determination on the wearing state of the user.

Figure 7:
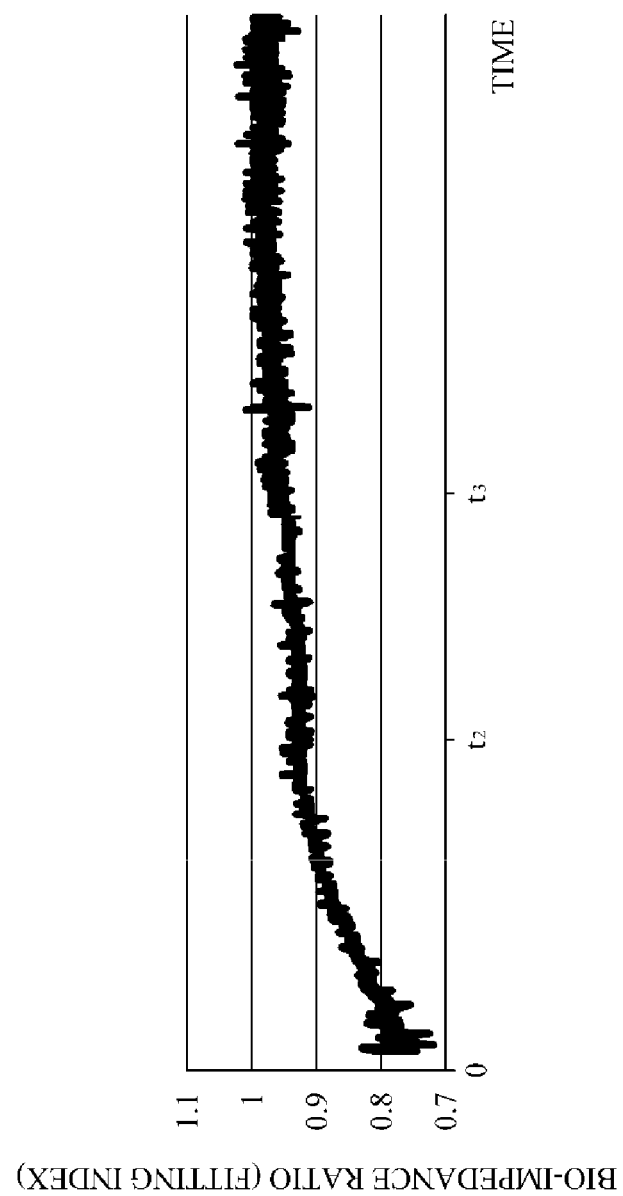
FIG. 7 is a graph showing a variation in bio-impedance ratio that may occur when the user is wearing the wearable device of FIG. 5A.

FIG. 7 is a graph showing a variation in a bio-impedance ratio that may occur when the user is wearing the wearable device 600 of FIG. 5A. The bio-impedance ratio may be a fitting index.

Referring to FIG. 7, it appears that the size of the fitting index gradually increases until time $t_2$ because the time of wearing and the variation in size is relatively large. During this period of time, the processor 640 of the wearable device 600 may generate information for guiding the wearing to guide the user to re-wear or appropriately wear the wearable device 600. In addition, the processor 600 may determine that the biometric information detected is valid after time $t_2$ when the fitting index becomes quite constant or time $t_3$ when the fitting index becomes completely constant is reached. A time point as a criterion for determining the validity of the biometric information detected may vary according to exemplary embodiments. In the case in which the biometric sensor 620 measures a biometric signal and estimates biometric information by applying a predetermined correlation model of the measured biometric signal and the biometric information, the correlation model may be updated with only the data that have been measured because time $t_2$ or time $t_3$.

In addition, the exemplary embodiments may also be implemented through computer-readable code and/or instructions on a medium, e.g., a computer-readable medium, to control at least one processing element to implement any above-described exemplary embodiments.

The medium may correspond to any medium or media that may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to exemplary embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

The foregoing exemplary embodiments are examples and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for biometric information detection, the apparatus comprising:
    a housing;
    a biometric sensor disposed on a surface of the housing, and configured to detect biometric information of a subject;
    an impedance measurer comprising a first biometric electrode pair and a second biometric electrode pair that are disposed around the biometric sensor, the first biometric electrode pair being different than the second biometric electrode pair, the first biometric electrode pair being configured to measure a first bio-impedance of the subject, and the second biometric electrode pair being configured to measure a second bio-impedance of the subject; and
    a processor configured to:
        determine a bio-impedance ratio of the first bio-impedance measured by the first biometric electrode pair to the second bio-impedance measured by the second biometric electrode pair; and
        determine validity of the detected biometric information, based on the determined bio-impedance ratio,
    wherein the biometric sensor is further configured to:
        estimate the biometric information by applying a predetermined correlation model to a biometric signal; and
        update the predetermined correlation model, based on the estimated biometric information in response to a sequential change in the determined bio-impedance ratio reaching a first predetermined range.

2. The apparatus of claim 1, wherein the processor is further configured to determine that the detected biometric information is valid in response to a size of the determined bio-impedance ratio being within a second predetermined range or the sequential change in the determined bio-impedance ratio being within a third predetermined range.

3. The apparatus of claim 1, wherein the first biometric electrode pair and the second biometric electrode pair are disposed symmetrically with respect to the biometric sensor.

4. The apparatus of claim 3, wherein the first biometric electrode pair is disposed along a direction perpendicular to a direction along which the second biometric electrode pair is disposed.

5. The apparatus of claim 3, wherein the first biometric electrode pair is disposed along a direction along which the biometric sensor is disposed.

6. The apparatus of claim 1, wherein the biometric sensor comprises an optical signal detector configured to:
    radiate light to the subject; and
    receive an optical signal returning from the subject, and
    the processor is further configured to estimate the biometric information, based on the received optical signal.

7. The apparatus of claim 6, wherein the processor is further configured to determine that the received optical signal or the estimated biometric information, estimated by the processor, is valid in response to the determined bio-impedance ratio being within a fourth predetermined range.

8. The apparatus of claim 6, wherein the processor is further configured to determine that the received optical signal or the estimated biometric information, estimated by the processor, is valid in response to the sequential change in the determined bio-impedance ratio reaching a fifth predetermined range.

9. A method for biometric information detection, the method comprising:
    detecting biometric information of a subject, using a biometric sensor contacting the subject;
    measuring a first bio-impedance of the subject, using a first biometric electrode pair contacting the subject;
    measuring a second bio-impedance of the subject, using a second biometric electrode pair contacting the subject, the second biometric electrode pair being different than the first biometric electrode pair;
    determining a bio-impedance ratio of the first bio-impedance measured by the first biometric electrode pair to the second bio-impedance measured by the second biometric electrode pair; and
    determining validity of the detected biometric information, based on the determined bio-impedance ratio,
    wherein the detecting biometric information of the subject further comprises:
    estimating the biometric information by applying a predetermined correlation model to a biometric signal; and
    updating the predetermined correlation model, based on the estimated biometric information in response to a sequential change in the determined bio-impedance ratio reaching a predetermined range.

10. A wearable device comprising:
    a housing;
    a wearing member connected to the housing, and configured to allow a user to wear the wearable device;
    a biometric sensor disposed on a surface of the housing, the surface contacting the user, and the biometric sensor being configured to detect biometric information of the user;
    an impedance measurer comprising a reference electrode pair and a measurement electrode pair that are disposed on the surface of the housing, the reference electrode pair being different than the measurement electrode pair, the reference electrode pair being configured to measure a first bio-impedance of the user, and the measurement electrode pair being configured to measure a second bio-impedance of the user; and
    a processor configured to:

determine a bio-impedance ratio of the first bio-impedance measured by the reference electrode pair to the second bio-impedance measured by the measurement electrode pair;

determine validity of the detected biometric information, based on the determined bio-impedance ratio, determine a state in which the user is wearing the wearable device, based on the determined bio-impedance ratio; and generate information for guiding the user to correct the determined state in response to a result of the determination of the state.

11. The wearable device of claim 10, wherein the reference electrode pair is disposed along a first direction that is a longitudinal direction of a body part on which the user wears the wearable device.

12. The wearable device of claim 11, wherein the body part is one of an arm, a leg, a finger, a toe, a neck, and a torso.

13. The wearable device of claim 11, wherein the reference electrode pair is disposed symmetrically with respect to the biometric sensor.

14. The wearable device of claim 13, wherein the measurement electrode pair is disposed along a second direction perpendicular to the first direction.

15. The wearable device of claim 14, wherein the measurement electrode pair is disposed symmetrically with respect to the biometric sensor.

16. The wearable device of claim 15, wherein the impedance measurer further comprises a second measurement electrode pair disposed along a third direction and a third measurement electrode pair disposed along a fourth direction, the second measurement electrode pair and the third measurement electrode pair being disposed symmetrically with respect to the biometric sensor, and the third direction forming an angle of 45 degrees with respect to the first direction, forming an angle of 45 degrees with respect to the second direction, and being perpendicular to the fourth direction.

17. The wearable device of claim 10, wherein the reference electrode pair is disposed along a direction perpendicular to a direction along which the wearing member extends from the housing, and the measurement electrode pair is disposed along a same direction as the direction along which the wearing member extends from the housing.

18. The wearable device of claim 10, wherein the processor is further configured to determine that the detected biometric information is valid in response to a size of the determined bio-impedance ratio or a sequential change in the determined bio-impedance ratio being within a predetermined range.

19. The wearable device of claim 10, further comprising any one or any combination of an audio output interface, a display, and a communicator that are disposed in the housing, and configured to output information that is generated based on the determined bio-impedance ratio.

20. The wearable device of claim 10, wherein the biometric sensor comprises an optical signal detector configured to:

radiate light to skin of the user; and receive an optical signal returning from the skin, and the processor is further configured to estimate the biometric information, based on the received optical signal.

21. The wearable device of claim 20, wherein the processor is further configured to determine that the received optical signal or the estimated biometric information, estimated by the processor, is valid in response to the determined bio-impedance ratio being within a predetermined range.

22. The wearable device of claim 20, wherein the processor is further configured to determine that the received optical signal or the estimated biometric information, estimated by the processor, is valid in response to a sequential change in the determined bio-impedance ratio reaching a predetermined range.

23. An apparatus for biometric information detection, the apparatus comprising:

a housing;

a biometric sensor disposed on a surface of the housing, and configured to detect biometric information of a subject;

an impedance measurer comprising first biometric electrodes and second biometric electrodes that are disposed on the surface of the housing, the first biometric electrodes being different than the second biometric electrodes, the first biometric electrodes being configured to measure a first bio-impedance of the subject, and the second biometric electrodes being configured to measure a second bio-impedance of the subject; and a processor configured to:

determine a bio-impedance ratio of the first bio-impedance measured by the first biometric electrodes to the second bio-impedance measured by the second biometric electrodes; and determine whether the detected biometric information is valid, based on the determined bio-impedance ratio, wherein the biometric sensor is further configured to:

estimate the biometric information by applying a predetermined correlation model to a biometric signal; and update the predetermined correlation model, based on the estimated biometric information in response to a sequential change in the determined bio-impedance ratio reaching a predetermined range.

24. The apparatus of claim 23, wherein one of the first biometric electrodes is disposed on a first side of the biometric sensor, and another one of the first biometric electrodes is disposed on a second side of the biometric sensor, the second side being symmetrically opposite the first side.

25. The apparatus of claim 23, wherein one of the second biometric electrodes is disposed on a first side of the biometric sensor, and another one of the second biometric electrodes is disposed on a second side of the biometric sensor, the second side being symmetrically opposite the first side.

26. The apparatus of claim 23, wherein the first biometric electrodes and the second biometric electrodes are disposed along a first direction, and the impedance measurer further comprises third biometric electrodes disposed along a second direction, and fourth biometric electrodes disposed along a third direction, the second direction forming a first angle with respect to the first direction, and the third direction forming a second angle with respect to the first direction.

* * * * *